(12) United States Patent
Stensrud

(10) Patent No.: US 9,487,537 B2
(45) Date of Patent: Nov. 8, 2016

(54) SYNTHESIS OF ISOHEXIDE DICARBAMATES AND DERIVATIVES THEREOF

(71) Applicant: ARCHER DANIELS MIDLAND COMPANY, Decatur, IL (US)

(72) Inventor: Kenneth Stensrud, Decatur, IL (US)

(73) Assignee: Archer Daniels Midland Co., Decatur, IL (US)

( * ) Notice: Subject to any disclaimer, the term of this patent is extended or adjusted under 35 U.S.C. 154(b) by 0 days.

(21) Appl. No.: 14/781,364

(22) PCT Filed: May 7, 2014

(86) PCT No.: PCT/US2014/037047
§ 371 (c)(1),
(2) Date: Sep. 30, 2015

(87) PCT Pub. No.: WO2014/200636
PCT Pub. Date: Dec. 18, 2014

(65) Prior Publication Data
US 2016/0031842 A1 Feb. 4, 2016

Related U.S. Application Data

(60) Provisional application No. 61/833,951, filed on Jun. 12, 2013.

(51) Int. Cl.
C07D 307/42 (2006.01)
C07D 307/12 (2006.01)
C07D 493/04 (2006.01)
A61K 31/40 (2006.01)
C08G 71/04 (2006.01)
C08G 73/00 (2006.01)
A61K 47/26 (2006.01)
A61K 31/428 (2006.01)
A61K 31/343 (2006.01)

(52) U.S. Cl.
CPC ............ *C07D 493/04* (2013.01); *A61K 31/40* (2013.01); *C07D 307/12* (2013.01); *C07D 307/42* (2013.01); *C08G 71/04* (2013.01); *C08G 73/00* (2013.01); *A61K 31/343* (2013.01); *A61K 31/428* (2013.01); *A61K 47/26* (2013.01)

(58) Field of Classification Search
None
See application file for complete search history.

(56) References Cited

U.S. PATENT DOCUMENTS 3,073,848 A * 1/1963 Wasson ............... C07D 307/12 549/496
4,619,917 A * 10/1986 Lee ..................... C07F 9/65586 514/77
4,820,718 A * 4/1989 Tomesch ............. C07D 405/12 514/336

* cited by examiner

*Primary Examiner* — Zinna Northington Davis
(74) *Attorney, Agent, or Firm* — Vincent Kung

(57) ABSTRACT

Dicarbamates of the reduction products of 2-hydroxymethyl-5-furfural (HMF) and a method of preparing the same are described. The method involves reacting a mixture of an isohexide and a cynate salt in a non-aqueous solvent, with a miscible acid having a pKa of about 3.7 or less. The dicarbamates of HMF-reduction products can serve as precursor materials from which various derivative compounds can be synthesized.

13 Claims, No Drawings

SYNTHESIS OF ISOHEXIDE DICARBAMATES AND DERIVATIVES THEREOF

BENEFIT OF PRIORITY

The present application claims benefit of priority of International Application No. PCT/US2014/037047, filed May 7, 2014, which claims priority from U.S. Provisional Application No. 61/833,951, filed Jun. 12, 2013, the contents of which are herein incorporated.

FIELD OF INVENTION

The present invention relates to a synthesis of precursor compounds for polymers. In particular, the present invention pertains to a method for preparing dicarbamates of the reduction products of 2-hydroxymethyl-5-furfural (HMF) (i.e., furan-2,5-dimethanol (FDM) and bis(hydroxymethyl)-tetrahydrofuran (bHMTHF)), and derivative compounds of such dicarbamates.

BACKGROUND

Traditionally, polymers and commodity chemicals have been prepared from petroleum-derived feedstock. As petroleum supplies have become increasingly costly and difficult to access, interest and research has increased to develop renewable or "green" alternative materials from biologically-derived sources for chemicals that will serve as commercially acceptable alternatives to conventional, petroleum-based or -derived counterparts, or for producing the same materials as produced from fossil, non-renewable sources.

Carbohydrates or sugars are ubiquitous in agricultural materials, and hence are rational precursors for empirical innovations in the "green" materials area. Organic compounds that are readily derived from sugars include furans, robust cyclic ethers that possess structural features which can be useful for making certain polymers, pharmaceuticals, or solvents, among other industrial constituents.

A compound that has received considerable attention of late is 5-(hydroxymethyl)furfural (HMF), (Figure 1), a salient dehydration product of the abundant, inexpensive monosaccharide, fructose.

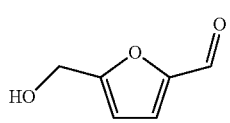

FIG. 1, Chemical structure of HMF

HMF is a versatile chemical antecedent to various furanic ring-based derivatives that are known intermediates for a multitude of chemical syntheses, and as plausible surrogates for aromatic hydrocarbons that derive from petroleum resources. Due to HMF's diverse functionalities, some have proposed that HMF be used to produce a wide range of commodities such as polymers, solvents, surfactants, pharmaceuticals, and plant protection agents. As alternates, derivatives of HMF are comparable to benzene-based aromatic compounds or to other compounds containing a furan or tetrahydrofuran (THF). HMF and 2,5-disubstituted furans and THF analogs, therefore, have great potential in the field of intermediate chemicals from renewable agricultural resources.

HMF itself, however, is rather unsuitable as a chemical intermediate substrate, given its propensity to decompose under thermo-oxidative conditions. Thus, one should look to derivatives of HMF for practical commercial utility. One derivative is furan-2,5-dimethanol (abbreviated as FDM, Scheme 1), which is produced from partial hydrogenation (aldehyde reduction) of HMF.

Scheme 1. - FDM B from partial hydrogenation of HMF A

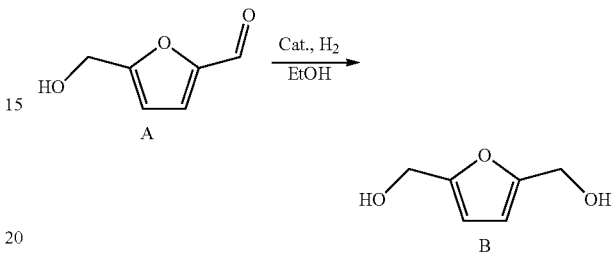

Other derivatives are 2,5-bis(hydroxymethyl)tetrahydrofuran (abbreviated as bHMTHF), saturated stereoisomeric analogs produced in a 9:1 cis (B):trans (C) diastereometic ratio when both the ring and aldehyde moieties of HMF are reduce completely (Scheme 2).

Scheme 2. - bHMTHFs from the exhaustive reduction of HMF

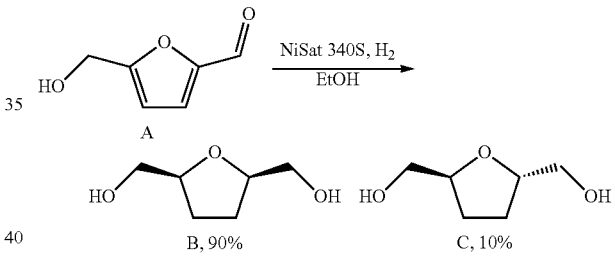

These materials can be of value as a molecular antecedent, for example, to polyesters, polyurethane foams, FDCA, plasticizers, additives, lubricants, and amphiphiles.

To become market competitive with petroleum products, however, the preparation of HMF derivatives from standard agricultural raw materials, such as sugars, need to become economically feasible in terms of cost. Heretofore, research for chemical derivatives using FDM and/or bHMTHFs has received limited attention due in part to the great cost and relative paucity (e.g., ~$200 per gram commercially) of the compounds. Recently, a need has arisen for a way to unlock the potential of FDM and bHMTHFs and their derivative compounds, as these chemical entities have gained attention as valuable glycolic antecedents for the preparation of polymers, solvents, additives, lubricants, and plasticizers, etc. Furthermore, the inherent, immutable chirality of bHMTHFs makes these compounds useful as potential species for pharmaceutical applications or candidates in the emerging chiral auxiliary field of asymmetric organic synthesis. Given the potential uses, a cost efficient and simple process that can synthesis derivatives from FDM and/or bHMTHFs would be appreciated by manufacturers of both industrial and specialty chemicals alike as a way to better utilize biomass-derived carbon resources.

SUMMARY OF THE INVENTION

The present invention relates, in part, to a method of synthesizing and isolating dicarbamate derivatives of the reduction products of 2-hydroxymethyl-5-furfural (HMF). The method involves providing a mixture of HMF-reduction products with a cyanate salt in an inert organic solvent, reacting the mixture with an acid having a $pK_a$ less than or equal to about 3.7. The reduction product of HMF is at least one of: a) furan-2,5-dimethanol (FDM) and b) (tetrahydrofuran-2,5-diyl)dimethanol (THF-diols). The acid is added to the reaction mixture at a controlled rate of about 0.03-0.1 stoichiometric equivalents per minute.

In another aspect, the present invention pertains to the dicarbamates of HMF-reduction products produced from the method.

In yet another aspect, the present invention pertains to processes for making certain derivatized materials that contain the dicarbamates of HMF-reduction products as structural precursors of non-polymer compounds, or as a monomer in either homopolymers or copolymers, and the derivative materials themselves.

DETAILED DESCRIPTION OF THE INVENTION

Section I

DEFINITION

As used herein the following definitions are applicable:

The term "monomer" refers to a repeating structural unit of polymer. A monomer typically is a lower molecular weight compound that can form covalent chemical bonds with other monomers, resulting in a polymer.

The term "polymer" refers to a compound comprising repeating structural units (monomers) connected by covalent chemical bonds, and which may include oligomers. Polymers may be derivatized (for example by hydrolysis), cross-linked, grafted, or end-capped. Non-limiting examples of polymers may include homopolymers, non-homopolymers, block copolymers, terpolymers, tetra-polymers, and homologues. A polymer may be a random, block, or an alternating polymer, or a polymer with mixed ransom, block, and/or alternating structure.

The term "homopolymer" refers to a polymer composed of a single type of repeating structural unit (monomers).

The term "non-homopolymer" refers to a polymer having more than one type of repeating structural units (monomers).

The term "copolymer" refers to a non-homopolymer composed of two or more types of repeating structural units (monomers), such as a "terpolymer" or "tetra-polymer," respectively, with three or four types of repeating structural units (monomers).

The term "derivative" refers to a material or chemical compound that is prepared as a secondary or tertiary reaction product from a primary structural substituent (for non-polymer compounds), or a monomer or polymer compound, in which the primary structural substituent, monomer or polymer has been modified in terms of either a functional group, structural moiety, or chemical linkage.

The term "water-tolerant Lewis acids" refers to a phenomenologic property of certain Lewis acid catalysts that are not deactivated by the presence of water, contrary to conventional Lewis acids that are summarily deactivated by reaction with water. Hence, a particular Lewis acid may show water tolerance for the purpose of one reaction, but not toward another reaction. (See e.g., S. Kobayashi, S. Nagayama, & T. Busujima, "Lewis Acid Catalysts Stable in Water: Correlation Between Catalytic Activity in Water and Hydrolysis Constants and Exchange Rate Constants for Substitution of Inner-Sphere Water Ligands," *J. Am. Chem. Soc.*, 120 (32): 8287-8288 (1998); S. Kobayashi & I. Hachiya, "Lanthanide Triflates as Water-Tolerant Lewis Acids: Activation of Commercial Formaldehyde Solution and Use in the Aldol Reaction of Silyl Enol Ethers with Aldehydes in Aqueous Media," *The Journal of Organic Chemistry*, 59 (13): 3590-3596, July 1994; N. A. Rebacz, "Hydration and Hydrolysis with Water Tolerant Lewis Acid Catalysis in High Temperature Water," Ph. D. Dissertation, University of Michigan (2011), the contents of which are incorporated herein by reference.)

Section II

DESCRIPTION

As biomass derived compounds that afford great potential as surrogates for non-renewable petrochemicals, FDM and bHMTHFs, the reduction products of HMF, are a class of bicyclic furanodiols that are valued as renewable molecular entities. As referred to above, these reduction products of HMF are versatile chemical platforms that have recently received interest because of their aromatic character (FDM) and intrinsic chiral bi-functionalities (bHMTHFs), which can permit a significant expansion of both existing and new derivative compounds that can be synthesized.

A.—Preparation of Dicarbamates of Reduction Products of HMF

The method for preparing dicarbamates of reduction products of HMF (i.e., FDM, THF-diols), as described herein, is a mild, high-yielding, single-step synthesis process. The process involves reacting a mixture of a HMF-reduction product and a cyanate salt in an inert organic solvent with an acid having a $pK_a$ of about 3.7 or less.

The present synthesis process can result in yields of corresponding dicarbamates of FDM and bHMTHFs, as demonstrated in the accompanying examples. The process is able to produce corresponding dicarbmates in reasonably high molar yields of at least 55% from the reduction products of HMF and cyanate starting materials, typically about 60% or 70% to about 75% or 80%. With proper control of the reaction conditions and time, one can achieve a yield of about 82%-95% or better of the dicarbamates.

The amount of cyanate salt used should be in excess of the amount of HMF-reduction products. The range of cyanate to FDM or bHMTHF ratio in terms of mole percent is a minimum of 2:1 (i.e., one cyanate per—OH group of a FDM or bHMTHF), and up to about 4:1 or 5:1 for purposes of practicality. (There is no theoretical maximum ratio, as once the reduction products of HMF forms the dicarbamate no further reactions will occur. However, the more unreacted salts that is present in the reaction, the more concern one may have in removing the salts subsequently during an aqueous wash.)

The reduction product of HMF is at least one of the following: FDM, bHMTHF, or a combination thereof. The respective reduction products of HMF can be obtained either commercially or synthesized from relatively inexpensive, widely-available biologically-derived feedstocks.

The cationic counter-ion to the cyanate salt is at least one of the following: Na, K, Li, Ag, Hg, Al, Ca, Mg, Pb, Sn, Ti, Ni, Cs, Rb, Cu, Zn, Cd, In, Co, Ga, Ba, Pd, Pt, Tl, Fr, Sb, Ge, Sr, Be, V, Bi, Mo, Mn, Fe, Nb, Cr, Eu, organic cations of ammonium, pyridinium, and/or a combination thereof.

The method uses a non-aqueous reaction system with an organic solvent that enables the reduction products of HMF to be soluble and reactive with the acid. The organic solvent can be at least one of the following: methylene chloride, chloroform, carbon tetrachloride, benzene, toluene, xylenes, linear and/or branched alkanes, tetrahydrofuran, 1,4-dioxane, dimethylsulfoxide, acetonitrile, dimethylformamide, acetic acid, HMPT, nitromethane, pyridine, N-methyl pyrolidinone, dimethylacetamide, ethyl acetate, acetone, methyl tert-butyl ether, diethyl ether.

An acid that is miscible or soluble in the organic solvent and having a pKa less than or equal to about 3.7 can be employed in the present synthesis. An acid having a pKa ≤3.7 will have a greater propensity to protonate the cyanate in situ to generate isosyanic acid, which is the active electrophilic species. The acid preferably has pKa of about 3.5 or less (e.g. about 2.5 or 2.7 to about 3.0 or 3.6; or about 2.6 or 2.8 to about 3.2 or 3.3) as in some examples. The acid can be either a) an organic acid or b) a mineral acid. Organic acids tend to have an enhanced solubility in an organic solvent (e.g., methylene chloride) which may make them more effective in the reaction; nevertheless, mineral acids can be just as effective. An organic acid can be: e.g., trifluoro-acetic acid (TFA), trichloro-acetic acid, oxalic acid, pyruvic acid, malonic acid, furamic acid, maleic acid, malic acid, tartaric acid, picric acid, electron deficient benzoic acids (mono, di, and tri-nitro, cyano, trifluoro), terephthalic acid, methanesulfonic acid, p-toluenesulfonic acid and trifluoromethylsulfonic acid. A mineral acid can be: e.g., sulfuric acid, hydrogen halides (HCl, HBr, HI), perchloric acid, phosphoric acid, and boric acid.

Introduction of the acid to the reaction system should be performed in a stead and controlled manner so as to maximize production of the target dicarbamate, while avoiding or minimizing the formation of undesired side products. The acid is added to the reaction mixture of FDM or bHMTHFs at a rate of about 0.03-0.1 stoichiometric equivalents per minute. Acids with a pKa of 3.5 or greater should be added slowly, because of the exothermic nature of the reaction.

One can execute the synthesis reaction in a single vessel under relatively mild conditions at a temperature of up to about 50° C. or 55° C. In general, the reaction is conducted at a starting temperature in a range from about 0° C. to about 30° C. or 40° C. More typically, the initial reaction temperature is in a range from about 10° C. to about 35° C. In certain embodiments, the reaction is performed at about ambient room temperature (i.e., ~18° C. to ~25° C.) to about 20° C. or 22° C. higher than room temperature. Because of its exothermic nature, the reaction can generate an additional 10° C.-15° C. of heat over and above the initial reaction temperature. This phenomenon permits the reaction to proceed at lower initial temperatures.

An advantage of the present process is that in excess amounts of cyanate, the reduction products of HMF converts substantially or completely to its dicarbamate species, minimizing waste and any remaining amount of unreacted starting materials in the final product mixture that may need separation. Another advantage of the present method is that the synthesis process requires minimal purification. As the dicarbamates are formed, they will precipitate from the homogeneous reaction mixture, and can be easily filtered to separate them from solution. One can further purify the FDM or bHMTHF dicarbamates using a variety of different techniques; for example, in a protocol that involves simple filtration, washing, and drying under high vacuum.

The process is able to produce dicarbamates of the reduction products of HMF in reasonably high molar yields of at least 55% from the bHMTHF starting materials, up to near quantitative yields. Typically yields range from about 60% to about 70%, or more typically about 68% or 75% to about 80% or 83%. With proper control of the reaction conditions and time, one can achieve a yield of about 85% to about 94% or 95% or better of the dicarbamate, such as demonstrated in the accompanying examples. Schemes 3 and 4, respectively, illustrate the general structures of the dicarbamate species of FDM and bHMTHFs.

Scheme 3:
Reaction of FDM with sodium isocyanate to generate FDM dicarbamate

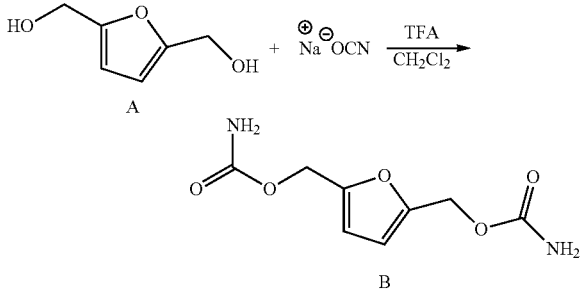

Scheme 4:
Reaction of bHMTHFs with sodium isocyanate to generate bHMTHF dicarbamates

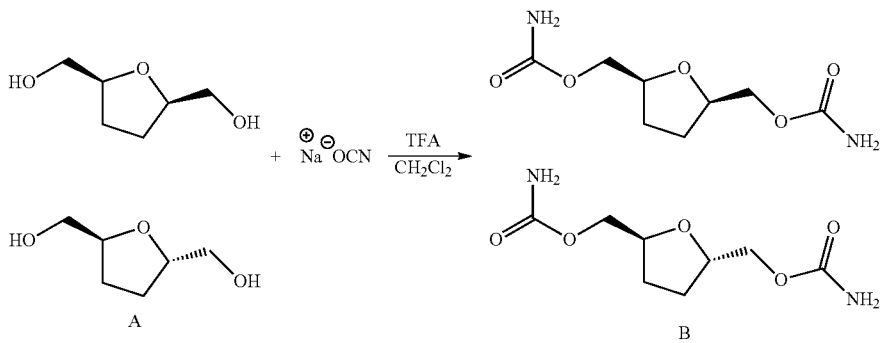

B.—Derivative Compounds of Dicarbamates of HMF-Reduction Products

Dicarbamates of HMF-reduction products can be useful and valuable precursor chemical compounds for a variety of Scheme 5: Synthesis of bHMTHF-dicarbamate derivates

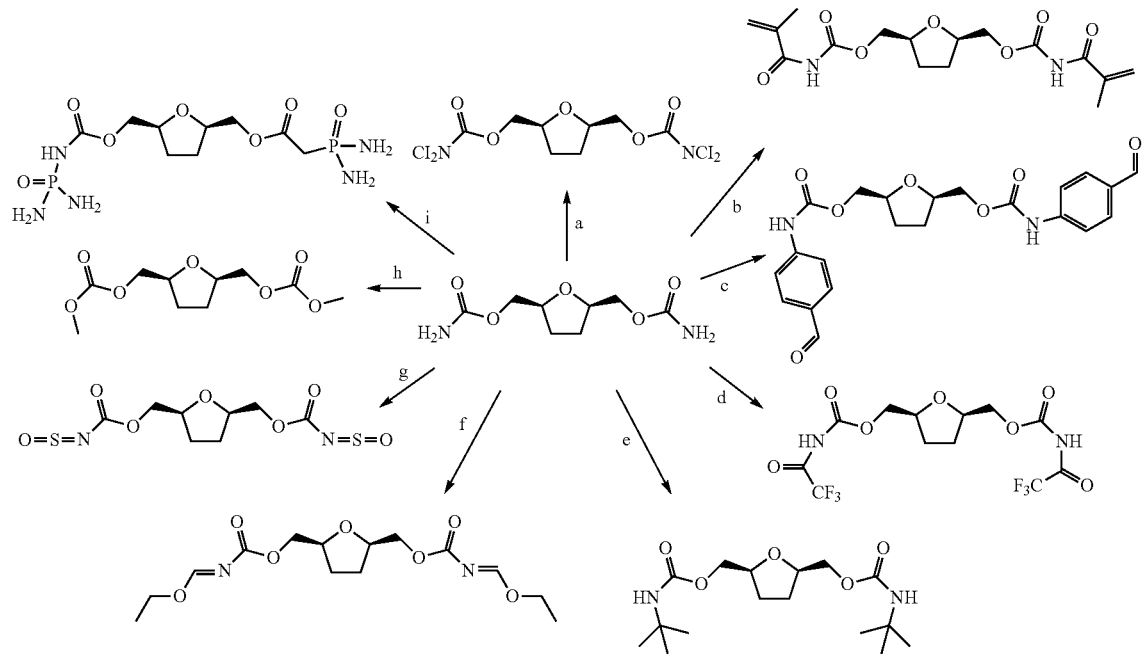

potential products, including for instance, a broad range of polymers (e.g., polyurethanes), chiral auxiliaries (e.g., for asymmetric synthesis used in pharmaceutical production), surfactants, or solvents. The present carbamate compounds can be adapted to serve as either a new, bio-derived monomer or a replacement for existing structurally analogous compounds, such as used in the pharmaceutical, personal care, or industrial chemical (derived from fossil hydrocarbons) industries.

Some of the uses to which carbamates can be adapted are illustrated generally in the following list, which includes examples of carbamates used as monomer units in various kinds of polymer compounds or compositions: 1) U.S. 2004/0087728 A1 or U.S. 2005/0080196 (a curable surface coating composition containing a carbamate functional addition polymer); 2) U.S. 2013/0090443 (polymerization of carbamate and thiocarbamate compounds for cosmetic, skin or hair care, or other personal care compositions); 3) U.S. 2002/0119320 or U.S. 2004/0236031 (coating composition containing a carbamate-functional group or resin); 4) U.S. Pat. No. 3,165,498 (polyfunctional interpolymers of olefinically unsaturated carbamates and olefins, which have a plurality of carbamate groups); or 5) U.S. 2012/0125800 (polymer with a polyester-carbamate backbone and one or more blocked isocyanate groups and coating composition).

Scheme 5, for example, presents several representative derivative compounds that may be made from bHMTHF dicarbamates. Although only the cis-species are depicted in the derivative synthesis diagram, the present reactions encompass both the cis- and trans-bHMTHF dicarbamate analog structures and derivative compounds, as well as similar reactions to prepare such derivative compounds are also contemplated herein.

Proceeding clockwise, each of the example reactions (a-i) shown in Scheme 5, can be executed respectively using, for instance, the following reagents:

a) for ((2R,5S)-tetrahydrofuran-2,5-diyl)bis(methylene)bis ((113-dichloranylidene)carbamate) and ((2S,5S)-tetrahydrofuran-2,5-diyl)bis(methylene)bis((113-dichloranylidene)carbamate): NaOCl, AcOH, $H_2O$;

b) for ((2R,5S)-tetrahydrofuran-2,5-diyl)bis(methylene)bis (methacryloylcarbamate) and ((2S,5S)-tetrahydrofuran-2, 5-diyl)bis(methylene)bis(methacryloylcarbamate): Methacryloyl chloride, t-BuOK, THF;

c) for ((2R,5S)-tetrahydrofuran-2,5-diyl)bis(methylene)bis ((4-formylphenyl)carbamate) and ((2S,5S)-tetrahydrofuran-2,5-diyl)bis(methylene)bis((4-formylphenyl)carbamate): p-bromobenzaldehyde, $Cs_2CO_3$, $Pd(OAc)_2$, 4,5-Bis(diphenylphosphino)-9,9-dimethylxanthene, THF;

d) for ((2R,5S)-tetrahydrofuran-2,5-diyl)bis(methylene)bis ((2,2,2-trifluoroacetyl)carbamate) and ((2S,5S)-tetrahydrofuran-2,5-diyl)bis(methylene)bis((2,2,2-trifluoroacetyl)carbamate): Trifluoroacetic anhydride, $Et_2O$;

e) for ((2R,5S)-tetrahydrofuran-2,5-diyl)bis(methylene)bis (tert-butylcarbamate) and ((2S,5S)tetrahydrofuran-2,5-diyl) bis(methylene)bis(tert-butylcarbamate): 2-Methylpropene, $BF_3$-$Et_2O$, $PhCH_3$;

f) for diethyl N',N'''-(((((2R,5S)-tetrahydrofuran-2,5-diyl)bis (methylene))bis(oxy))bis(carbonyl))(1E,1'E)-diformimidate and diethyl N',N''-(((((2S,5S)-tetrahydrofuran-2,5-diyl)bis(methylene))bis(oxy))-bis(carbonyl))(1E,1'E)-diformimidate: Triethyl orthoformate, BF$_3$-THF, THF;

g) for ((2R,5S)-tetrahydrofuran-2,5-diyl)bis(methylene)bis((oxo-γ$^4$-sulfanylidene)carbamate) and ((2S,5S)-tetrahydrofuran-2,5-diyl)bis(methylene)bis((oxo-γ$^4$-sulfanylidene)carbamate): SOCl$_2$;

h) for dimethyl (((2R,5S)-tetrahydrofuran-2,5-diyl)bis(methylene))bis(carbonate) and dimethyl(((2S,5S)-tetrahydrofuran-2,5-diyl)bis(methylene))bis(carbonate): Lewis acids (Bi(OTf)$_3$, Ga(OTf)$_3$, Sc(OTf)$_3$, In(OTf)$_3$, Cu(OTf)$_3$, Al(OTf)$_3$, Lanthanide triflates, CH$_3$OH, ~180-220° C.;

i) for ((2R,5S)-tetrahydrofuran-2,5-diyl)bis(methylene)bis((diaminophosphoryl)carbamate) and ((2S,5S)-tetrahydrofuran-2,5-diyl)bis(methylene)bis((diaminophosphoryl)carbamate): 1) PCl$_5$, CHCl$_3$; 2) H$_2$O, 0° C.; 3) NH$_3$, Et$_3$N, CHCl$_3$, reflux. The particular time and temperatures will vary for each of the reaction processes, and can be determined empirically.

Similarly, Scheme 6 illustrates several representative derivative compounds that can be synthesized from FDM dicarbamate using the same reagents as listed above.

As before, proceeding clockwise, each of the example reactions (a-i) shown in Scheme 6, can be prepared respectively using, for instance, the following reagents:

a) for furan-2,5-diylbis(methylene)bis((chloroimino)-13-chloranecarboxylate): NaOCl, AcOH, H$_2$O;

b) for furan-2,5-diylbis(methylene)bis(methacryloylcarbamate): Methacryloyl chloride, t-BuOK, THF;

c) for furan-2,5-diylbis(methylene)bis((4-formylphenyl)carbamate): p-bromobenzaldehyde, Cs$_2$CO$_3$, Pd(OAc)$_2$, 4,5-Bis(diphenylphosphino)-9,9-dimethylxanthene, THF;

d) for furan-2,5-diylbis(methylene)bis((2,2,2-trifluoroacetyl)carbamate): Trifluoroacetic anhydride, Et$_2$O;

e) for furan-2,5-diylbis(methylene)bis(tert-butylcarbamate): 2-Methylpropene, BF$_3$-Et$_2$O, PhCH$_3$;

f) for diethyl N',N''-(((furan-2,5-diylbis(methylene))bis(oxy))bis(carbonyl))(1E,1'E)-diformimidate: Triethyl orthoformate, BF$_3$-THF, THF;

g) for furan-2,5-diylbis(methylene)bis((oxo-γ$^4$-sulfanylidene)carbamate): SOCl$_2$;

h) for furan-2,5-diylbis(methylene)dimethyl bis(carbonate): Lewis acids (Bi(OTf)$_3$, Ga(OTf)$_3$, Sc(OTf)$_3$, In(OTf)$_3$, Cu(OTf)$_3$, Al(OTf)$_3$, Lanthanide triflates, CH$_3$OH, ~180-220° C.;

i) for furan-2,5-diylbis(methylene)bis((diaminophosphoryl)carbamate): 1) PCl$_5$, CHCl$_3$; 2) H$_2$O, 0° C.; 3) NH$_3$, Et$_3$N, CHCl$_3$, reflux.

Another example of a derivative synthesis reaction that employs the dicarbamates of reduction products of HMF Scheme 6:
Synthesis of FDM-Dicarbamate Derivatives

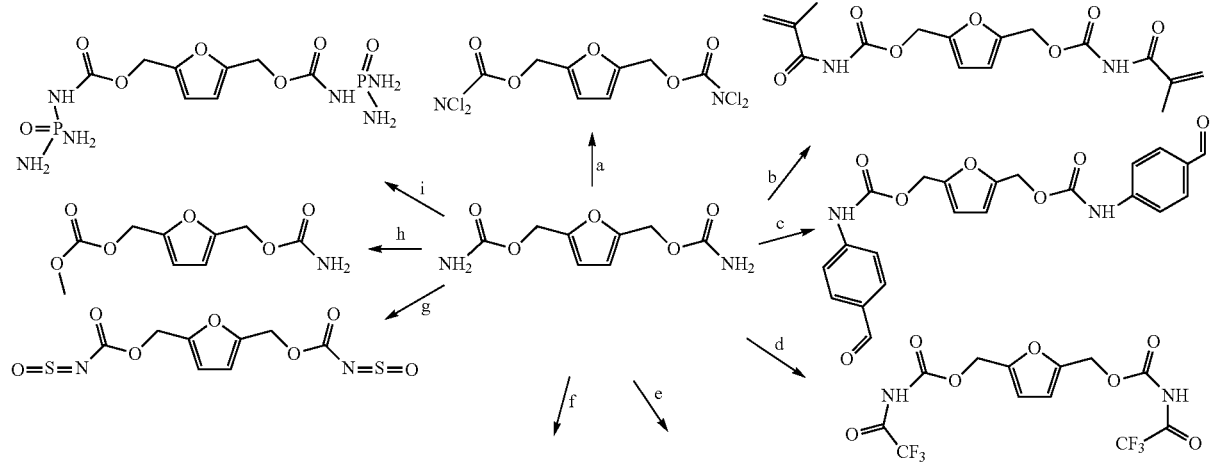

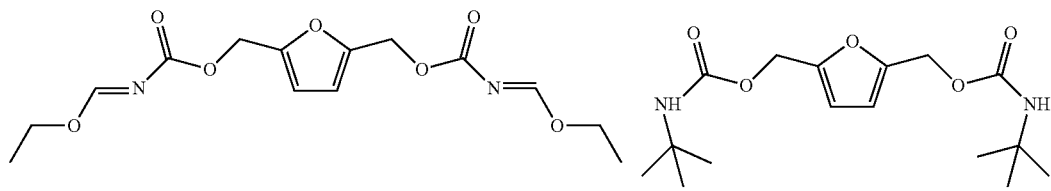

described herein is shown in Scheme 7 and 8 (FDM and bHMTHF, respectively), which involves preparing formaldehyde polymers. (The reactions are expounded further in the accompanying examples for derivative compounds in the Examples section, infra).

Scheme 7:
Synthesis of Formaldehyde Polymers of FDM Dicarbamates

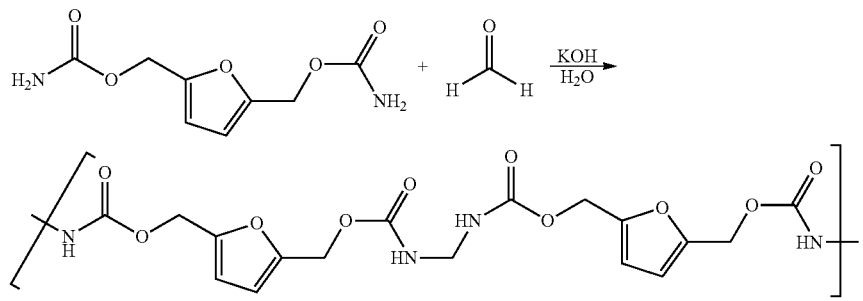

Scheme 8:
Synthesis of Formaldehyde Polymers of bHMTHF Dicarbamates

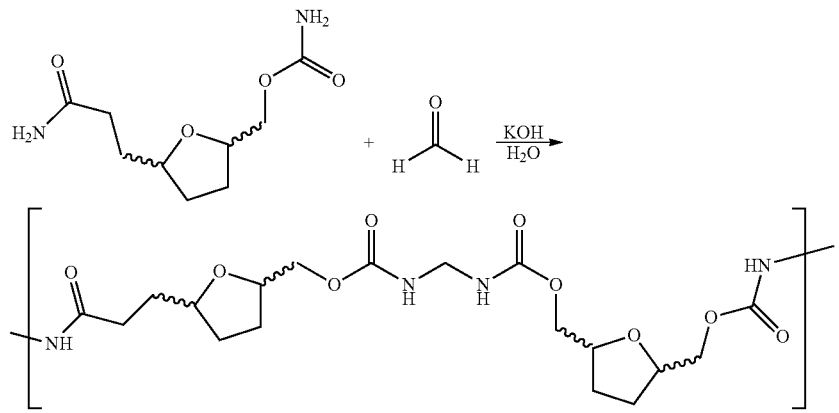

The formaldehyde-FDM and/or bHMTHF dicarbamate polymers would have applications (e.g., thermosetting resins) similar to, for instance, that described in U.S. 2009/0149608 (thermosetting resin composition with polycarbamate and polycarbamides reacted with formaldehyde), or Moon G. Kim, "Renewable Polyol-based Polycarbamates and Polycarbamate-Formaldehyde Thermosetting Resins," JOURNAL OF APPLIED POLYMER SCIENCE, 122(4), 2209-2220 (15 Jun. 2011), the contents of which are incorporated herein by reference.

Another possible useful application for the present dicarbamates of the reduction products of HMF can be as a monomer in an analogous method for crosslinking polyurethanes, such as described in U.S. 2011/0313091 (a crosslinked polyurethane composition having a polycarbamate as a first component and a polyaldehyde or acetal or hemiacetal thereof as a second component), the content of which is incorporated herein by reference.

Furthermore, N-acylated carbamates can be useful platforms in the synthesis of biologically active compounds. The preparation and use of these derivative compounds are described, for example, by Liu, Xue-Kui, et al., ORGANIC & BIOMOLECULAR CHEMISTRY (2012), 10(6), 1275-1284; Kuhakarn, Chutima et al., TETRAHEDRON LETTERS (2007), 48(46), 8182-8184; Brouillette, Wayne J. et al., JOURNAL OF ORGANIC CHEMISTRY (1979), 44(5), 839-43, or in U.S. Pat. No. 3,819,683, relating to aryl N-methyl-N-acylcarbamates, the contents of which are incorporated herein by reference.

As an illustration of an alternative embodiment of a method for making derivatives, Schemes 9 and 10, exhibits a general reaction for a Lewis-acid-(LA)-triflate-mediated N-acylation of FDM or bHMTHF dicarbamates. Although Lewis acids have been employed for situations like N-acylation (e.g., Reddy, Chada Raji, et al., ARCHIVE FOR ORGANIC CHEMISTRY (ARKIVOC) 2008 (ii) 250-257), none have involved water-tolerant triflates and/or use a low quantity (≤1 or 2 mol. %) catalyst load (e.g., about 0.01 mol. % to about 1.5 mol. %) as in the present method and examples. In the present reactions, effective catalyst loads can range from as little as about 0.005 or 0.035 mol. % up to about 4 or 5 mol. %. Reaction times will tend to be longer with lower amounts, which can afford some degree of control in the reaction.

Scheme 9: N-acylation of FDM dicarbamates

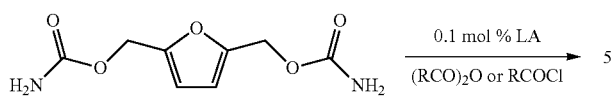

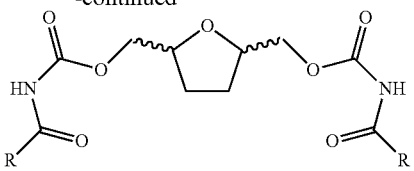

LA = Sc(OTf)$_3$, Bi(OTf)$_3$, Ga(OTf)$_3$, In(OTf)$_3$, Al(OTf)$_3$, Sn(OTf)$_3$
R = Alkyl, Aryl, Allyl LA = Sc(OTf)$_3$, Bi(OTf)$_3$, Ga(OTf)$_3$, In(OTf)$_3$, Al(OTf)$_3$, Sn(OTf)$_3$
R = Alkyl, Aryl, Allyl Scheme 10: N-acylation of bHMTHF dicarbamates

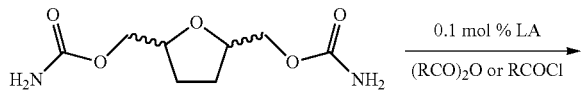

The Lewis-acid triflate is water-tolerant, and thus useful as a homogeneous catalyst in an aqueous milieu. That is in other words, the Lewis acid triflate exhibits a uniquely stable behavior in water, in that it only very slowly hydrolyzes, and thus retains its acidity for a protracted time period when in the presence of water. For example, aluminum triflate is a powerful Lewis acid in an aqueous environment; while in contrast, aluminum chloride will hydrolyze immediately forming hydroxyl groups, and lose all of its acidic capacity. It is believed that a role of the Lewis-acid triflate is in lowering the activation barrier of the acid chloride or anhydride by coordinating to the carbonyl moiety. This action promotes a supervening displacement by the moderately nucleophilic FDM or bHMTHF dicarbamate to generate the N-acylated carbamate derivative compounds.

Schemes 11 and 12 illustrate particular examples of this reaction, involving N-acylation of carbamates of the HMF-reduction products with the bio-based fatty acid, oleic acid.

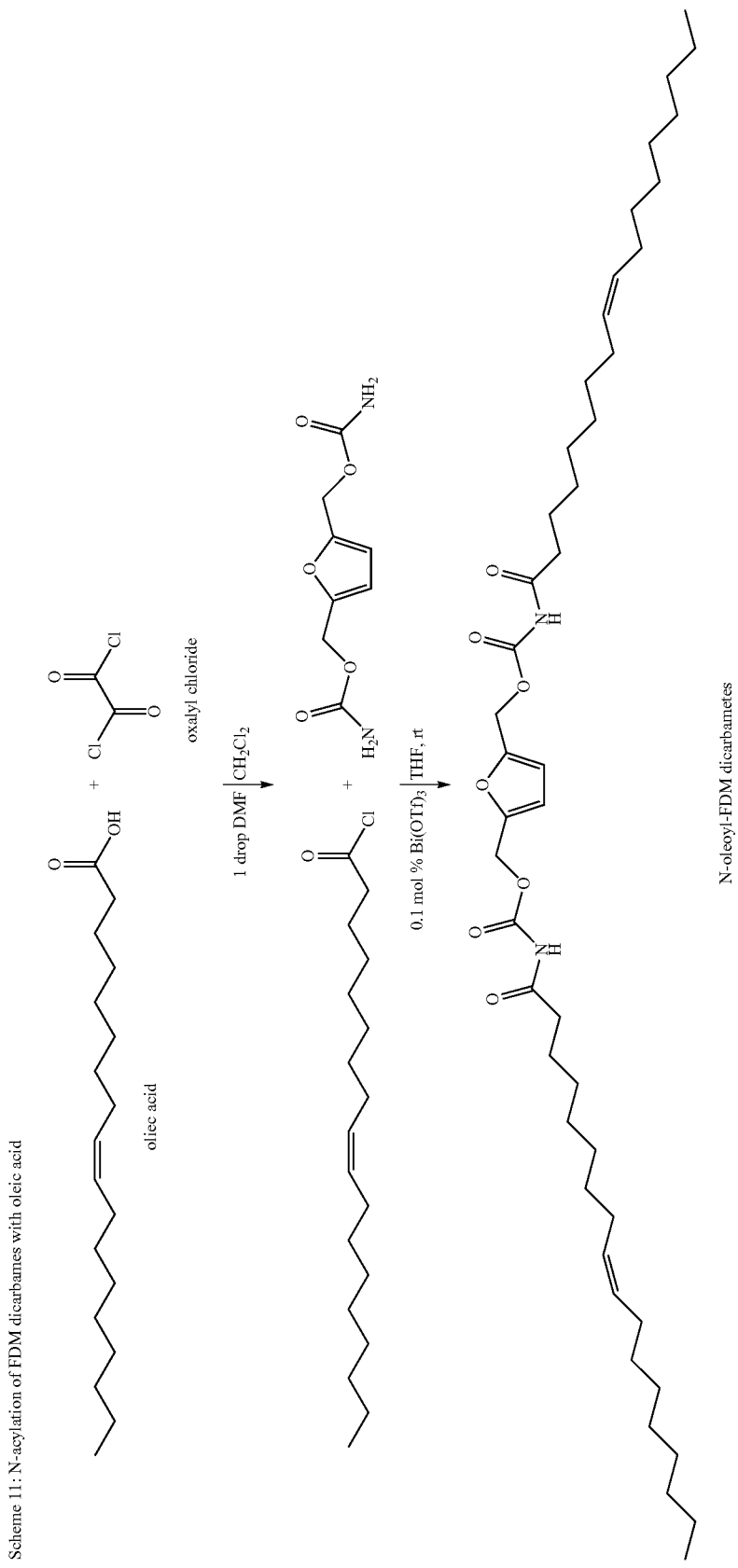

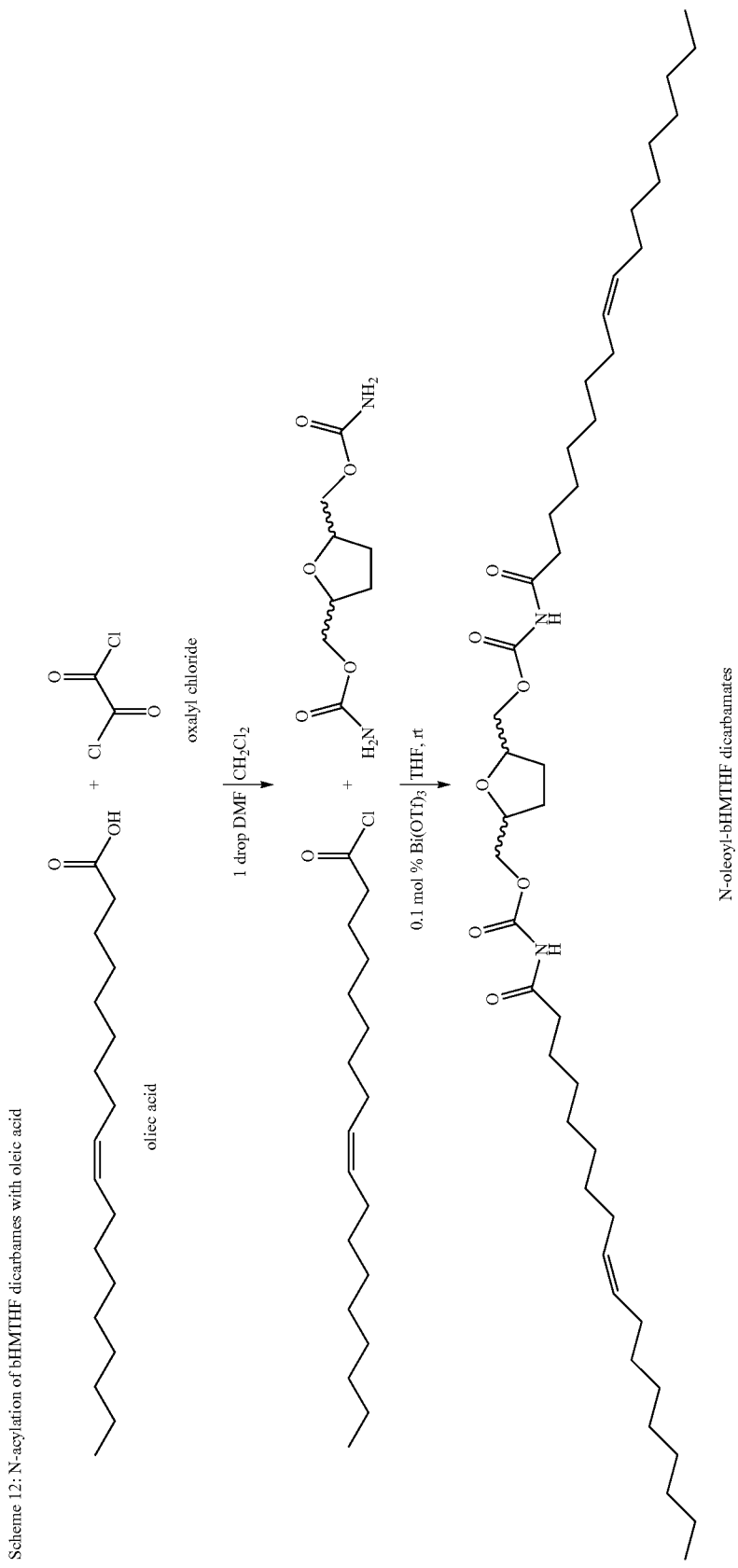

The preparation of various derivative compounds according to this method of reaction will be described more fully in the accompanying examples below. Note that excess reagents will tend to generate undesired side reactions under the conditions employed. Hence, the ratio of reagents should be kept in a range about 5:1 maximum ratio of formaldehyde to FDM or bHMTHF dicarbamate (Example 1, vide infra), or as in about 2:1 ratio for reagent to FDM, bHMTHF dicarbamate (Examples 3 and 4, vide infra). The specific yield of derivative compounds will depend on the particular reactions. Typically, the yield of target derivative compound can range from at least about 50% or 55% up to about 93% or 97% or better.

Section III

EXAMPLES

The present invention is further illustrated with reference to the following examples.

A. Dicarbamates

Example 1

Synthesis of furan-2,5-diylbis(methylene)dicarbamate, B

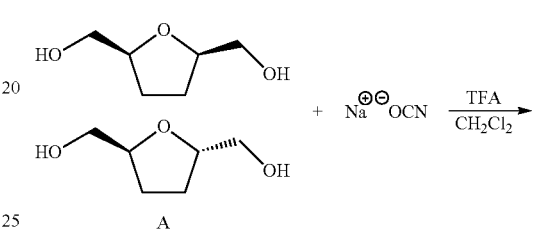

Experimental: A two neck, 50 mL round bottomed flask was charged with 1 g of FDM A (7.55 mmol), 1.97 g of sodium cyanate (30.2 mmol) and 20 mL of anhydrous methylene chloride resulting in a suspension. The necks were then stoppered with rubber septa, one with a thermocouple insert that immersed in the solution. While stirring, 2.32 mL of trifluoroacetic acid was added via syringe dropwise over 5 minutes. The temperature of the solution warmed from 25° C. to 41° C. over 15 minutes and solids disappeared. After about 30 minutes, a white precipitate formed, which was filtered and analyzed as only byproduct sodium trifluoroacetate by $^{13}$C NMR (D$_2$O, 2000 scans) no residual FDM was espied). The supernatant was concentrated in vacuo, affording B as a pale yellow solid that weighed 1.55 g (93% of theoretical). $^{13}$C NMR (CDCl$_3$, 100 MHz) δ (ppm) 151.61, 147.38, 113.57, 61.11 (notable FDM signals at 154.27, 108.79, 57.76 ppm absent).

Example 2

Synthesis of ((2R,5S)-tetrahydrofuran-2,5-diyl)bis(methylene) dicarbamate and diastereomer, B

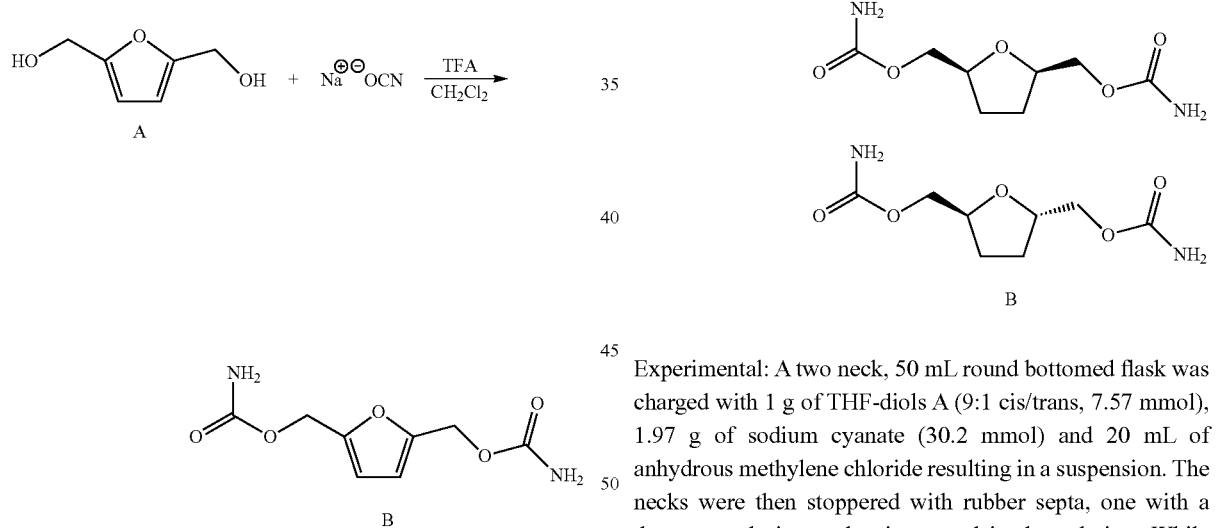

Experimental: A two neck, 50 mL round bottomed flask was charged with 1 g of THF-diols A (9:1 cis/trans, 7.57 mmol), 1.97 g of sodium cyanate (30.2 mmol) and 20 mL of anhydrous methylene chloride resulting in a suspension. The necks were then stoppered with rubber septa, one with a thermocouple insert that immersed in the solution. While stirring, 2.32 mL of trifluoroacetic acid was added via syringe dropwise over 5 minutes. The temperature of the solution warmed from 25° C. to 41° C. over 15 minutes and solids disappeared. After about 30 minutes, a white precipitate formed, which was filtered, dried and determined to be byproduct sodium trifluoroacetate by $^{13}$C NMR (D$_2$O, 2000 scans) no residual FDM was espied). The supernatant was concentrated in vacuo, affording B as a loose, clear oil that weighed 1.42 g (86% of theoretical). $^{13}$C NMR (CDCl$_3$, 100 MHz) δ (ppm) 157.39, 77.79, 69.37, 27.45 (characteristic THF-Diol (meso, cis) signals at 80.46, 64.94, 27.67 ppm absent)

B. Derivatives Compounds

I. Derivatives of bHMTHFs Dicarbamates

Example 1

Synthesis of bHMTHF (9:1 cis/trans) Dicarbamate-Formaldehyde polymers

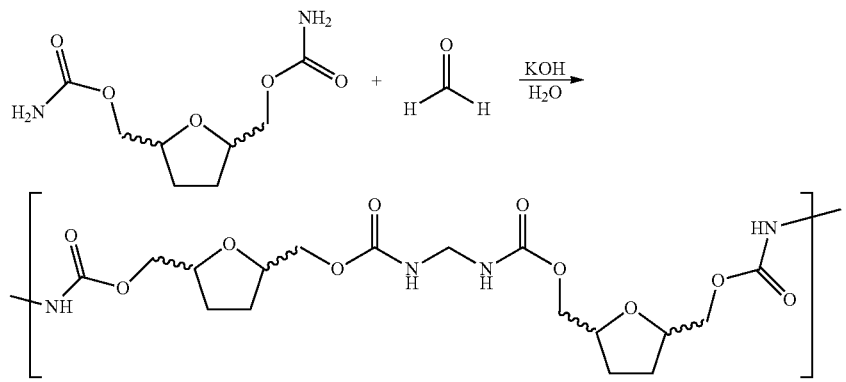

Experimental: A single neck, 50 mL round bottomed flask equipped with a ½" PTFE coated magnetic stir bar was charged with 300 mg of a 50% solution of formaldehyde (5 mmol), 219 mg of bHMTHF dicarbamates (9:1 cis/trans, 1 mmol), 500 mL of water, and 1 N aqueous KOH until the pH was 8.5. While stirring, the resultant suspension was heated to 85° C.; after 45 min, the solution opacity disappeared, and the reaction continued for 30 more min. After this time, the pH was adjusted to 1.5 with 1N HCl and reaction proceeded until a viscosity change was apparent, at which time the reaction was culminated by cooling and pH adjusting to 8 with 1N KOH. Here the residual solids are measured.

Example 2

Synthesis of (tetrahydrofuran-2,5-diyl)bis(methylene)bis(acetylcarbamate), 9:1 mixture of cis and trans diastereomers

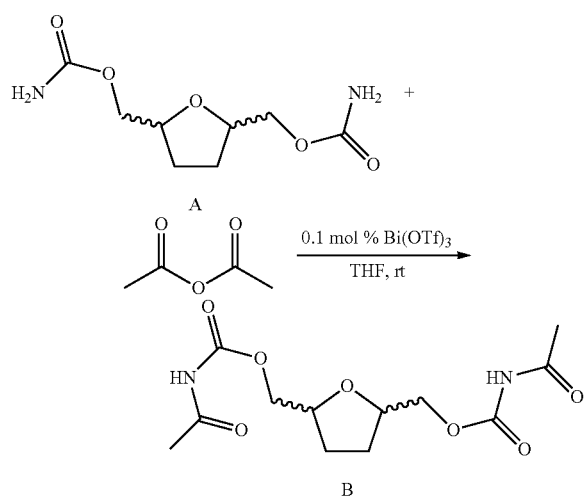

Experimental: A 10 mL round bottomed flask equipped with a ¼" PTFE coated magnetic stir bar was charged with 250 mg of bHMTHF dicarbamates A (9:1 cis/trans, 1.14 mmol), 56 µg of Sc(OTf)$_3$ (0.1 mol %) and 2 mL of anhydrous THF. While stirring, 251 µL of acetic anhydride (2.51 mmol) was added dropwise over 15 minutes. The solution was observed to warm considerably with each drop. After the entire volume had been added, the mixture continued to stir at room temperature for an additional 5 hours. An aliquot was removed and spotted on a normal phase TLC plate, which revealed overlapping bands (cerium molybdate illumination, Rf=0.44, 0.45) after development in 100% EtOAc. The signature bands corresponding to the 9:1 cis/trans mixture of A, Rf=0.29, 0.30 were noticeably absent, indicating full conversion of these starting materials. Solids were then filtered and excess solvent was then evaporated under reduced pressure, affording 321 mg (93% of theory) of B as a colorless oil, that analyzed by $^{13}$C NMR (100 MHz, d$^6$-DMSO) as δ (ppm) 170.0, 169.4 152.8, 152.5, 82.0, 81.6, 74.5, 67.2, 66.9, 30.5, 30.2, 24.1, 23.9 ppm.

Example 3

Synthesis of (tetrahydrofuran-2,5-diyl)bis(methylene)bis(benzoylcarbamate), 9:1 mixture of cis and trans diastereomers

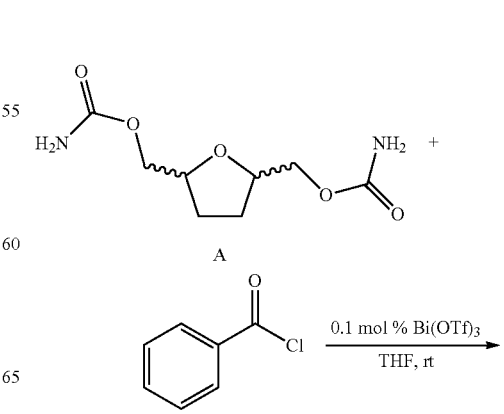

-continued

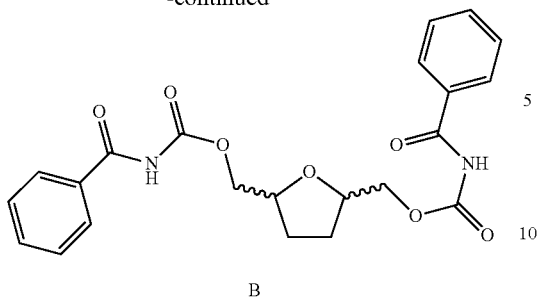

B

Experimental: A 10 mL round bottomed flask equipped with a ¼" PTFE coated magnetic stir bar was charged with 250 mg of bHMTHF dicarbamates A (9:1 cis/trans 1.14 mmol), 75 µg of Bi(OTf)$_3$ (0.1 mol %) and 2 mL of anhydrous THF. While stirring, 291 µL of benzoyl chloride (2.51 mmol) was added dropwise over 15 minutes. The solution was observed to warm considerably with each drop. After the entire volume had been added, the mixture continued to stir at room temperature for an additional 5 hours. An aliquot was removed and spotted on a normal phase TLC plate, which revealed two overlapping bands (UV-Vis illumination, Rf=0.50, 0.51) after development in 100% EtOAc. The signature bands corresponding to A, Rf=0.29, 0.30 were noticeably absent, adducing that A had fully converted. Solids were then filtered and excess solvent was then evaporated under reduced pressure, affording 366 mg (86% of theoretical) of a B as a colorless oil, analyzed by $^{13}$C NMR (100 MHz, d$^6$-DMSO) δ (ppm) 155.5, 155.3, 139.1, 138.8, 129.5, 129.2, 127.4, 127.2, 123.2, 123.0, 85.6, 85.2, 67.8, 67.5, 30.7, 30.5 ppm.

Example 4

Synthesis of (tetrahydrofuran-2,5-diyl)bis(methylene)bis(acryloylcarbamate), 9:1 mixture of cis and trans diastereomers

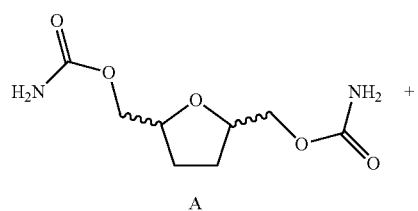

A

Experimental: A 10 mL round bottomed flask equipped with a ¼" PTFE coated magnetic stir bar was charged with 250 mg of bHMTHF dicarbamates A (9:1 cis/trans 1.14 mmol), 64 µg of In(OTf)$_3$ (0.1 mol %) and 2 mL of anhydrous THF. While stirring, 204 µL of propenoyl chloride (2.51 mmol) was carefully added, dropwise over 15 minutes. The solution was observed to warm considerably with each drop. After the entire volume had been added, the mixture continued to stir at room temperature for an additional 6 hours. An aliquot was removed and spotted on a normal phase TLC plate, which revealed two overlapping bands (cerium molybdate illumination, Rf=0.46, 0.47) after development in 100% EtOAc. The signature bands corresponding to A, Rf=0.29, 0.30 were noticeably absent, adducing that A had fully converted. Solids were then filtered and excess solvent was then evaporated under reduced pressure, affording 338 mg (90% of theoretical) of B a colorless oil, analyzed by $^{13}$C NMR (100 MHz, d$^6$-DMSO) δ (ppm) 170.2, 170.0, 153.4, 153.1, 132.5, 132.4, 128.3, 128.0, 84.1, 83.9, 66.9, 66.6, 28.7, 28.4 ppm.

II Derivatives of FDM Dicarbamates

Example 1

Synthesis of FDM Dicarbamate-Formaldehyde polymers

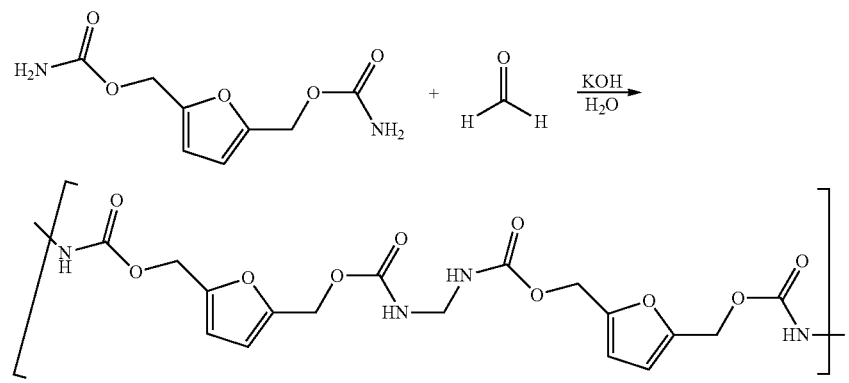

Experimental: A single neck, 50 mL round bottomed flask equipped with a ½" PTFE coated magnetic stir bar was charged with 300 mg of a 50% solution of formaldehyde (5 mmol), 214 mg of bHMTHF dicarbamates (1 mmol), 500 mL of water, and 1 N aqueous KOH until the pH was 8.5. While stirring, the resultant suspension was heated to 85° C.; after 45 min, the solution opacity disappeared, and the reaction continued for 30 more min. After this time, the pH was adjusted to 1.5 with 1N HCl and reaction proceeded until a viscosity change was apparent, at which time the reaction was culminated by cooling and pH adjusting to 8 with 1N KOH. Here the residual solids are measured.

Example 2

Synthesis of furan-2,5-diylbis(methylene)bis(acetylcarbamate)

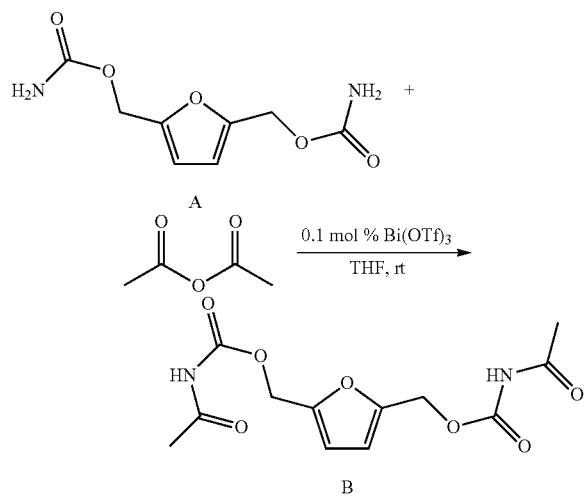

Experimental: A 10 mL round bottomed flask equipped with a ¼" PTFE coated magnetic stir bar was charged with 250 mg of FDM dicarbamates A (9:1 cis/trans, 1.17 mmol), 58 µg of Sc(OTf)$_3$ (0.1 mol %) and 2 mL of anhydrous THF. While stirring, 257 µL of acetic anhydride (2.58 mmol) was added dropwise over 15 minutes. The solution was observed to warm considerably with each drop. After the entire volume had been added, the mixture continued to stir at room temperature for an additional 5 hours. An aliquot was removed and spotted on a normal phase TLC plate, which revealed a single band (cerium molybdate illumination, Rf=0.42) after development in 100% EtOAc. The signature band corresponding to the FDM-dicarbamate A Rf=0.27 was noticeably absent, indicating full conversion of these starting materials. Solids were then filtered and excess solvent was then evaporated under reduced pressure, affording 315 mg (91% of theory) of B as a white solid material that analyzed by $^{13}$C NMR (100 MHz, d$^6$-DMSO) as δ (ppm) 170.5, 153.1, 140.3, 109.2, 57.0, 22.9.

Example 3

Synthesis of furan-2,5-diylbis(methylene)bis(benzoylcarbamate)

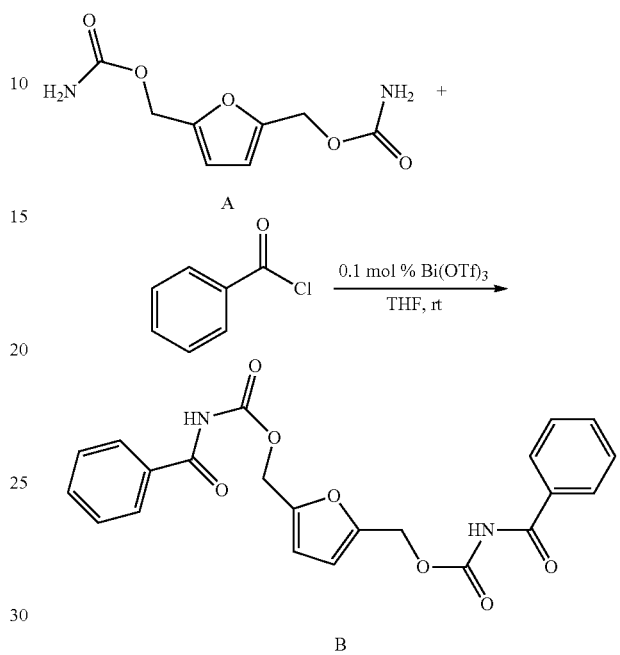

Experimental: A 10 mL round bottomed flask equipped with a ¼" PTFE coated magnetic stir bar was charged with 250 mg of bHMTHF dicarbamates A (9:1 cis/trans 1.17 mmol), 79 µg of Bi(OTf)$_3$ (0.1 mol %) and 2 mL of anhydrous THF. While stirring, 300 µL of benzoyl chloride (2.58 mmol) was added dropwise over 15 minutes. The solution was observed to warm considerably with each drop. After the entire volume had been added, the mixture continued to stir at room temperature for an additional 5 hours. An aliquot was removed and spotted on a normal phase TLC plate, which revealed a single band (UV-Vis illumination, Rf=0.46) after development in 100% EtOAc. The signature bands corresponding to A, Rf=0.27 was noticeably absent, adducing that A had fully converted. Solids were then filtered and excess solvent was then evaporated under reduced pressure, affording 381 mg (89% of theoretical) of B as a light yellow solid, analyzed by $^{13}$C NMR (100 MHz, d$^6$-DMSO) δ (ppm) 155.2, 141.6, 139.7, 129.6, 129.1, 122.7, 108.3, 58.0.

Example 4

Synthesis of furan-2,5-diylbis(methylene)bis(acryloylcarbamate)

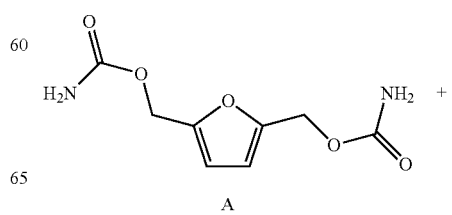

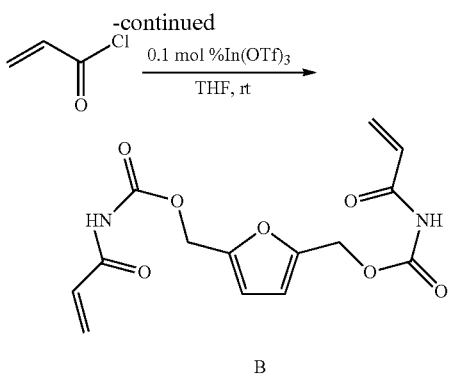

Experimental: A 10 mL round bottomed flask equipped with a ¼" PTFE coated magnetic stir bar was charged with 250 mg of FDM dicarbamates A (1.17 mmol), 70 µg of In(OTf)$_3$ (0.1 mol %) and 2 mL of anhydrous THF. While stirring, 212 µL of propenyl chloride (2.58 mmol) was carefully added, dropwise over 15 minutes. The solution was observed to warm considerably with each drop. After the entire volume had been added, the mixture continued to stir at room temperature for an additional 6 hours. An aliquot was removed and spotted on a normal phase TLC plate, which revealed a single band (cerium molybdate illumination, Rf=0.43) after development in 100% EtOAc. The signature band corresponding to A, Rf=0.27 was noticeably absent adducing that A had fully converted. Solids were then filtered and excess solvent was then evaporated under reduced pressure, affording 346 mg (92% of theoretical) of B as a white solid, analyzed by $^{13}$C NMR (100 MHz, d$^6$-DMSO) δ (ppm) 170.2, 153.0, 141.2, 132.6, 127.3, 107.9, 57.0.

Although the present invention has been described generally and by way of examples, it is understood by those persons skilled in the art that the invention is not necessarily limited to the embodiments specifically disclosed, and that modifications and variations can be made without departing from the spirit and scope of the invention. Thus, unless changes otherwise depart from the scope of the invention as defined by the following claims, they should be construed as included herein.

We claim:

1. A process for preparing dicarbamates of reduction products of HMF, the process comprising: providing a mixture of a HMF-reduction product with a cyanate salt in an inert organic solvent, reacting said mixture with an acid having a pK$_a$≤3.7.

2. The process according to claim 1, wherein said acid is added to said reaction mixture of HMF-reduction products at a rate of about 0.03-0.1 stoichiometric equivalents per minute.

3. The process according to claim 1, wherein said HMF-reduction product is at least: a) FDM and b) THF-diols.

4. The process according to claim 1, wherein said organic solvent is at least: methylene chloride, chloroform, carbon tetrachloride, benzene, toluene, xylenes, linear and/or branched alkanes, tetrahydrofuran, 1,4-dioxane, dimethyl-sulfoxide, acetonitrile, dimethylformamide, acetic acid, HMPT, nitromethane, pyridine, N-methyl pyrolidinone, dimethylacetamide, ethyl acetate, acetone, methyl tert-butyl ether, and diethyl ether.

5. The process according to claim 1, wherein said cyanate salt having a cationic counter-ion selected from the group consisting of: Na, K, Li, Ag, Hg, Al, Ca, Mg, Pb, Sn, Ti, Ni, Cs, Rb, Cu, Zn, Cd, In, Co, Ga, Ba, Pd, Pt, Tl, Fr, Sb, Ge, Sr, Be, V, Bi, Mo, Mn, Fe, Nb, Cr, Eu, organic cations of ammonium, pyridinium, and a combination of the foregoing.

6. The process according to claim 1, wherein said acid is either an organic acid or a mineral acid.

7. The process according to claim 6, wherein when said acid is an organic acid, said acid is at least: trifluoro-acetic acid (TFA) trichloro-acetic acid, oxalic acid, pyruvic acid, malonic acid, furamic acid, maleic acid, malic acid, tartaric acid, picric acid, electron deficient benzoic acids (mono, di, and tri-nitro, cyano, trifluoro), terephthalic acid, methanesulfonic acid, p-toluenesulfonic acid, and trifluoromethylsulfonic acid.

8. The process according to claim 6, wherein when said acid is a mineral acid, said acid is at least: sulfuric acid, hydrogen halide, perchloric acid, phosphoric acid, and boric acid.

9. The process according to claim 1, wherein said reaction is conducted at a temperature in a range from about 0° C. to about 55° C.

10. The process according to claim 1, further comprising purifying said dicarbamates of HMF-reduction products, according to a protocol involving a simple filtration, washing, and drying under high vacuum.

11. The process according to claim 1, wherein said process results in at least a 55% yield of corresponding dicarbamates of HMF-reduction products.

12. The process according to claim 11, wherein said process results in about a 70% or greater yield of corresponding dicarbamates of HMF-reduction products.

13. The process according to claim 8, wherein said hydrogen halide is selected from: HCl, HBr, and HI.

* * * * *